US007544756B2

(12) United States Patent
Shah et al.

(10) Patent No.: US 7,544,756 B2

(45) Date of Patent: Jun. 9, 2009

(54) CROSSLINKED POLYMERS WITH AMINE BINDING GROUPS

(75) Inventors: Rahul R. Shah, Woodbury, MN (US); Karl E. Benson, St. Paul, MN (US); Charles M. Leir, Falcon Heights, MN (US); George G. I. Moore, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 658 days.

(21) Appl. No.: 11/240,239

(22) Filed: Sep. 30, 2005

(65) Prior Publication Data

US 2007/0078244 A1 Apr. 5, 2007

(51) Int. Cl.
*C08F 226/06* (2006.01)
*C08F 132/08* (2006.01)

(52) U.S. Cl. ....................... 526/259; 526/258; 526/286; 526/288; 526/323.1; 526/323.2

(58) Field of Classification Search ................. 526/258, 526/259, 286, 288, 323.1, 323.2
See application file for complete search history.

(56) References Cited

U.S. PATENT DOCUMENTS 6,513,897 B2 2/2003 Tokie
6,696,157 B1 2/2004 David et al.
6,765,036 B2 7/2004 Dede et al.
6,897,164 B2 5/2005 Baude et al.
7,423,155 B2 * 9/2008 Benson et al. ............. 546/219
2002/0128340 A1 9/2002 Young et al.
2005/0070627 A1 3/2005 Falsafi et al.
2005/0113477 A1 5/2005 Oxman et al.

FOREIGN PATENT DOCUMENTS

WO WO 03/014072 2/2003

OTHER PUBLICATIONS

Lui et al., "Surface-Reactive Acrylic Copolymer for Fabrication of Microfluidic Devices", Analytical Chemistry, 2005, pp. A-H.

* cited by examiner

*Primary Examiner*—Helen L. Pezzuto
(74) *Attorney, Agent, or Firm*—Jean A. Lown

(57) ABSTRACT

Crosslinked polymeric materials are described that contain pendant amine capture groups. The amine capture groups include N-sulfonyldicarboximide groups that can react with amine-containing materials by a ring opening reaction. Reaction mixtures used to prepare the crosslinked polymeric materials, articles containing the crosslinked polymeric materials, methods of making articles, and methods of immobilizing an amine-containing material are also described.

10 Claims, No Drawings

CROSSLINKED POLYMERS WITH AMINE BINDING GROUPS

TECHNICAL FIELD

Crosslinked polymeric materials having pendant amine capture groups, articles containing the crosslinked polymeric materials, and methods of immobilizing an amine-containing material are described.

BACKGROUND

Amine-containing materials such as amine-containing analytes, amino acids, DNA, RNA, proteins, cells, tissue, organelles, immunoglobins, or fragments thereof immobilized on a surface can be used in numerous applications. For example, immobilized biological amines can be used for the medical diagnosis of a disease or genetic defect, for biological separations, or for detection of various biomolecules. Immobilization of the amine containing material is typically accomplished by reaction of an amino group with an amine reactive functional group that is covalently attached to the surface of the substrate.

Such amine reactive surfaces can be prepared, for example, by coating onto the surface of a substrate a solution of a polymeric material prepared from an amine reactive monomer such as N-[(meth)acryloxy]succinimide or vinyl azlactone. An amine-containing material can react with the N-acyloxysuccinimide group resulting in displacement of N-hydroxysuccinimide and formation of a carboxamide. An amine-containing material can react with the cyclic azlactone resulting in an opening of the ring structure.

Although polymeric surfaces that include a reactive functional group such as an N-acyloxysuccinimide group or an azlactone group can react readily with primary or secondary amine-containing materials, such reactive functional groups can suffer from a number of disadvantages. For example, many of the reactions with biological amines are conducted in dilute aqueous solutions. Under these conditions, the N-acyloxysuccinimide functional group is known to undergo rapid hydrolysis. This competing reaction can cause incomplete or inefficient immobilization of the amine-containing materials on the substrate.

While azlactone functional groups are more stable to hydrolysis, it is difficult to synthesize an azlactone linked to any polymerizable group other than a vinyl group. This results in polymeric material with the amine reactive functional group directly attached to the polymer backbone. This can make it difficult for the amine containing material to get close enough to the amine reactive group for efficient immobilization.

A need exists for polymeric materials with alternative amine reactive functional groups that can be used as coatings for the immobilization of amine-containing materials and that have good adhesion to a substrate.

SUMMARY

Reaction mixtures and crosslinked polymeric materials formed from the reaction mixtures are described. More specifically, the reaction mixtures and the crosslinked polymeric materials contain amine capture groups. The amine capture groups include N-sulfonyldicarboximide groups that can react with amine-containing materials by a ring opening reaction. Articles containing the crosslinked polymeric material, methods of making the articles, and methods of immobilizing an amine-containing material are also described.

In a first aspect, a reaction mixture is described that includes (a) an amine capture monomer of Formula I

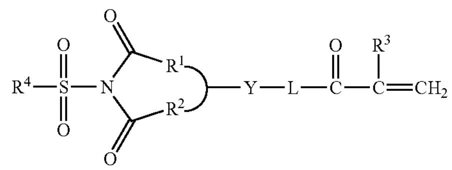

and (b) a crosslinking monomer that includes at least two (meth)acryloyl groups. The amine capture monomer of Formula I can be unsubstituted or substituted with a halo, alkyl, alkoxy, or combinations thereof. In Formula I, L is an oxy or —NR$^6$—;

R$^1$ and R$^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

R$^3$ is hydrogen or methyl;

R$^4$ is an alkyl, aryl, aralkyl, or —N(R$^5$)$_2$, wherein each R$^5$ is an alkyl group or both R$^5$ groups taken together with the nitrogen atom to which they are attached form a four to eight membered heterocyclic group;

R$^6$ is hydrogen, alkyl, aryl, aralkyl, acyl, alkylsulfonyl, or arylsulfonyl; and Y is a single bond or a divalent group comprising an alkylene, heteroalkylene, arylene, or combinations thereof.

In a second aspect, a crosslinked polymeric material is described that includes the reaction product of a reaction mixture that contains (a) an amine capture monomer of Formula I and (b) a crosslinking monomer that includes at least two (meth)acryloyl groups.

In a third aspect, an article is described that includes a substrate and a crosslinked polymeric material disposed on a surface of the substrate. The crosslinked polymeric material includes the reaction product of a reaction mixture that contains (a) an amine capture monomer of Formula I and (b) a crosslinking monomer that includes at least two (meth)acryloyl groups. The crosslinked polymeric material has a pendant amine capture group that includes a N-sulfonyldicarboximide group.

In a fourth aspect, a method of making an article is described. The method includes providing a substrate, disposing a reaction mixture on a surface of the substrate, and curing the reaction mixture to form a crosslinked polymeric material. The reaction mixture contains (a) an amine capture monomer of Formula I and (b) a crosslinking monomer that includes at least two (meth)acryloyl groups. The crosslinked polymeric material has a pendant amine capture group that includes a N-sulfonyldicarboximide group.

In a fifth aspect, a method of immobilizing an amine-containing material is described. The method includes providing a substrate, and disposing a reaction mixture on a surface of the substrate. The reaction mixture contains (a) an amine capture monomer of Formula I and (b) a crosslinking monomer that includes at least two (meth)acryloyl groups. The method further includes curing the reaction mixture to form a crosslinked polymeric material having a pendant amine capture group that includes a N-sulfonyidicarboximide group, and reacting an amine-containing material with the N-sulfonyidicarboximide group.

In a sixth aspect, a polymeric material is provided that includes pendant groups of Formula II

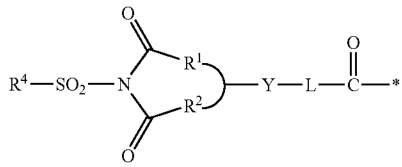

wherein

L is an oxy or —$NR^6$—;

$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

$R^4$ is an alkyl, aryl, aralkyl, or —$N(R^5)_2$, wherein each $R^5$ is an alkyl group or both $R^5$ groups taken together with the nitrogen atom to which they are attached form a four to eight membered heterocyclic group;

$R^6$ is hydrogen, alkyl, aryl, aralkyl, acyl, alkylsulfonyl, or arylsulfonyl;

Y is a single bond or a divalent group comprising an alkylene, heteroalkylene, arylene, or combinations thereof;

an asterisk (*) denotes an attachment site of the pendant group to a backbone of the polymeric material;

the pendant group of Formula II is unsubstituted or substituted with a halo, alkyl, alkoxy, or combinations thereof; and the polymeric material is crosslinked.

In a seventh aspect, a polymeric material is provided that includes pendant groups of Formula III

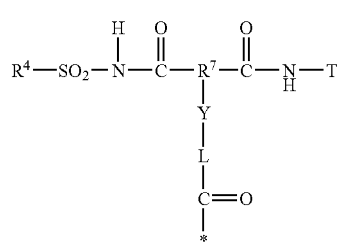

wherein

L is an oxy or —$NR^6$—;

$R^4$ is an alkyl, aryl, aralkyl, or —$N(R^5)_2$, wherein each $R^5$ is an alkyl group or both $R^5$ groups taken together with the nitrogen atom to which they are attached form a four to eight membered heterocyclic group;

$R^6$ is hydrogen, alkyl, aryl, aralkyl, acyl, alkylsulfonyl, or arylsulfonyl;

$R^7$ is an alkylene having 1 to 5 carbon atoms, aromatic group, saturated or unsaturated cyclic group, saturated or unsaturated bicyclic group, or combination thereof;

T is equal to a primary amine-containing biological material minus a —$NH_2$ group;

Y is a single bond or a divalent group comprising an alkylene, heteroalkylene, arylene, or combinations thereof;

an asterisk (*) denotes an attachment site of the pendant group to a backbone of the polymeric material;

the pendant group of Formula II is unsubstituted or substituted with a halo, alkyl, alkoxy, or combinations thereof, and the polymeric material is crosslinked.

The terms "a", "an", and "the" are used interchangeably with "at least one" to mean one or more of the elements being described.

The term "acyl" refers to a monovalent group of formula —(CO)R where R is an alkyl group and where (CO) used herein indicates that the carbon is attached to the oxygen with a double bond.

The term "alkoxy" refers to a monovalent group of formula —OR where R is an alkyl group.

The term "alkyl" refers to a monovalent group that is a radical of an alkane and includes groups that are linear, branched, cyclic, or combinations thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene typically has 1 to 30 carbon atoms. In some embodiments, the alkylene contains 1 to 20, 1 to 10, 1 to 8, 1 to 6, or 1 to 4 carbon atoms. The radical centers of the alkylene can be on the same carbon atom (i.e., an alkylidene) or on different carbon atoms.

The term "alkylsulfonyl" refers to a monovalent group of formula —$SO_2R$ where R is an alkyl.

The term "amine capture monomer" refers to a monomer having an amine capture group. The term "amine capture" refers to a group on a monomer or polymeric material that is capable of reacting with an amine-containing material. The amine capture group often includes a N-sulfonyidicarboximide group.

The term "amine-containing material" refers to a material that has a primary amine group, a secondary amine group, or a combination thereof. The amine-containing material can be a biological material or a non-biological material. The amine-containing material often has an alkylene group attached to the primary amine group, secondary amine group, or a combination thereof.

The term "aralkyl" refers to a monovalent group that is a radical of the compound R—Ar where Ar is an aromatic carbocyclic group and R is an alkyl group.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "arylsulfonyl" refers to a monovalent group of formula —$SO_2Ar$ where Ar is an aryl.

The term "arylene" refers to a divalent group that is carbocyclic and aromatic. The group has one to five rings that are connected, fused, or combinations thereof The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "carbonyl" refers to a divalent group of formula —(CO)—.

The term "carbonylimino" refers to a divalent group of formula —(CO)NR$^b$— where $R^b$ is hydrogen, alkyl, aryl, aralkyl, acyl, arylsulfonyl, or alkylsulfonyl.

The term "carbonyloxy" refers to a divalent group of formula —(CO)O—.

The term "dicarboximide" refers to a trivalent group of formula

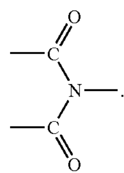

The term "halo" refers to fluoro, bromo, chloro, or iodo.

The term "heteroalkylene" refers to a divalent alkylene having one or more —$CH_2$— groups replaced with a thio, oxy, or —NR$^a$— where $R^a$ is hydrogen or alkyl. The heteroalkylene can be linear, branched, cyclic, or combinations thereof and can include up to 60 carbon atoms and up to 15 heteroatoms. In some embodiments, the heteroalkylene includes up to 50 carbon atoms, up to 40 carbon atoms, up to 30 carbon atoms, up to 20 carbon atoms, or up to 10 carbon atoms.

The term "(meth)acrylate" refers to monomer that is an acrylate or methacrylate. Likewise, the term "(meth)acrylamide" refers to a monomer that is an acrylamide or a methacrylamide.

The term "(meth)acryloyl" group refers to an ethylenically unsaturated group of formula $CH_2$=CR$^c$—(CO)— where $R^c$ is hydrogen or methyl.

The term "N-sulfonyldicarboximide" refers to a trivalent entity of formula

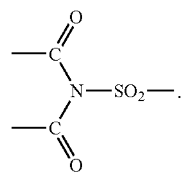

The term "oxy" refers to a divalent group of formula —O—.

The term "pendant" when referring to a polymeric material means a group that is attached to the backbone of the polymeric material but that is not part of the backbone of the polymeric material. The pendant group is not involved in the polymerization reaction. For example, the group Q is the pendant group in a polymer formed by free radical polymerization of a reaction mixture that includes ethylenically unsaturated monomers of formula $CH_2$=C($R^x$)-Q. In this monomer formula, $R^x$ is a hydrogen, alkyl, or aryl and Q is a group attached to the ethylenically unsaturated group.

The term "polymer" refers to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like.

The term "thio" refers to a divalent group of formula —S—.

The term "room temperature" refers to a temperature of about 20° C. to about 25° C. or about 22° C. to about 25° C.

A curve connecting two groups in a formula indicates that the two groups together form part of a structure that can be cyclic. That is, the two groups are linked together. A line intersecting this curve indicates a covalent bond to an atom in the structure.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Reaction mixtures used to prepare crosslinked polymeric materials, crosslinked polymeric materials formed from the reaction mixtures, articles containing the crosslinked polymeric materials, methods of making the articles, and methods of immobilizing amine-containing materials are described. More specifically, the reaction mixtures include (a) a monomer having an amine capture group and (b) a crosslinking monomer. The crosslinked polymeric material has a pendant amine capture group that includes a N-sulfonyldicarboximide group capable of reacting with an amine-containing material by a ring opening reaction.

A reaction mixture is provided that includes (a) an amine capture monomer of Formula I

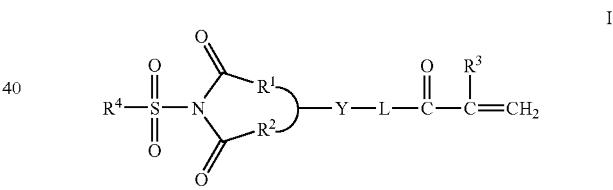

I and (b) a crosslinking monomer that includes at least two (meth)acryloyl groups. The monomer of Formula I can be unsubstituted or substituted with a halo, alkyl, alkoxy, or combinations thereof. In Formula I, L is an oxy or —NR$^6$—;

$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

$R^3$ is hydrogen or methyl;

$R^4$ is an alkyl, aryl, aralkyl, or —N($R^5$)$_2$ wherein each $R^5$ are each an alkyl group or taken together with the nitrogen atom to which they are attached form a four to eight membered heterocyclic group;

$R^6$ is hydrogen, alkyl, aryl, aralkyl, acyl, alkylsulfonyl, or arylsulfonyl; and Y is a single bond or a divalent group selected from an alkylene, heteroalkylene, arylene, or combinations thereof.

The amine capture monomer of Formula I can be a (meth) acrylate monomer when L is oxy as shown in Formula I(a).

I(a)

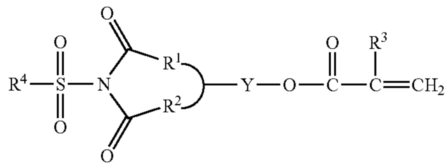

Some exemplary monomers are acrylates (i.e., where $R^3$ is hydrogen) or methacrylates (i.e., where $R^3$ is methyl).

The amine capture monomer of Formula I can be a (meth) acrylamide monomer when L is —$NR^6$— as shown in Formula I(b).

I(b)

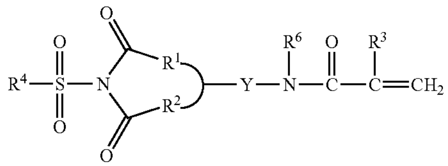

Some exemplary monomers are acrylamides (i.e., where $R^3$ is hydrogen) or methacrylamides (i.e., where $R^3$ is methyl).

Group Y can be a single bond or can be a divalent group that includes an alkylene, heteroalkylene, arylene, or combinations thereof. The divalent group Y can further include optional groups selected from a carbonyl, carbonylimino, carbonyloxy, oxy, thio, —$NR^6$—, or combinations thereof. Group Y and the combined group —Y-L- typically do not include peroxide groups (i.e., two oxy groups bonded together).

Group Y can be an alkylene group or Y can include an alkylene connected to at least one other group selected from another alkylene, heteroalkylene, arylene, carbonyl, carbonyloxy, carbonylimino, oxy, thio, —$NR^3$—, or combination thereof. In other examples, Y can be a heteroalkylene group or Y can include a heteroalkylene connected to at least one other group selected from another heteroalkylene, alkylene, arylene, carbonyl, carbonyloxy, carbonylimino, oxy, thio, —$NR^6$—, or combination thereof. In still other examples, Y can be an arylene group or Y can include an arylene connected to at least one other group selected from another arylene, alkylene, heteroalkylene, carbonyl, carbonyloxy, carbonylimino, oxy, thio, —$NR^6$—, or combination thereof.

In some exemplary monomers of Formula I, group Y can include a carbonyloxy, or carbonylimino group attached to an alkylene such as in the monomer of the following formula

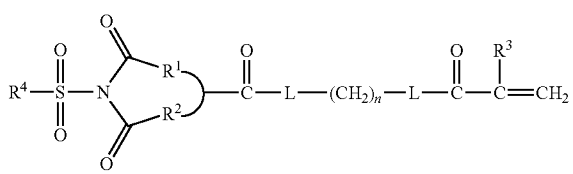

where n is an integer of 1 to 30. The groups $R^1$, $R^2$, $R^3$, $R^4$, and L are the same as described for Formula I. In some monomers, n is no greater than 20, no greater than 10, no greater than 8, no greater than 6, or no greater than 4. The monomers can be unsubstituted or substituted with a halo, alkyl, alkoxy, or combinations thereof.

In other examples where Y includes a first alkylene group that is connected to a second alkylene group or to a first heteroalkylene group with a group selected from a carbonyl, carbonyloxy, carbonylimino, oxy, thio, or —$NR^6$—. Additional alkylene or heteroalkylene groups can be connected to the second alkylene group or the first heteroalkylene group with a group selected from a carbonyl, carbonyloxy, carbonylimino, oxy, thio, or —$NR^6$—.

Group Y can be a heteroalkylene as in the following formula

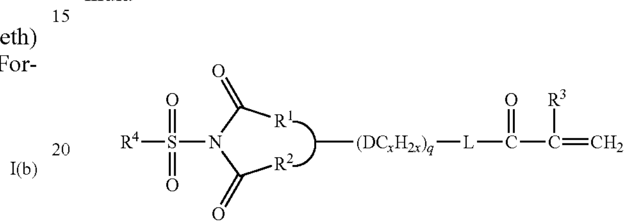

or group Y can be a heteroalkylene attached to another group such as a carboxy or carbonylimino as in the following formula

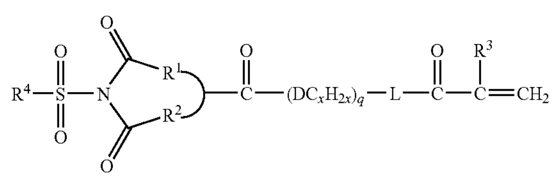

In these formulas, q is an integer of 1 to 15; x is an integer of 2 to 4; and D is oxy, thio, or —NH—. The groups $R^1$, $R^2$, $R^3$, $R^4$, and L are the same as previously defined for Formula I. Exemplary compounds include those where q is an integer no greater than 12, no greater than 10, no greater than 8, no greater than 6, no greater than 4, or no greater than 2; and x is no greater than 3, or equal to 2. The compounds can be unsubstituted or substituted with a halo, alkyl, alkoxy, or combinations thereof.

In other exemplary monomers of Formula I, group Y includes a first heteroalkylene group that is connected to a second heteroalkylene or to a first alkylene group with a group selected from a carbonyl, carbonyloxy, carbonylimino, oxy, thio, or —$NR^6$—. Additional alkylene or heteroalkylene groups can be connected to the second heteroalkylene group or the first alkylene group with a group selected from a carbonyl, carbonyloxy, carbonylimino, oxy, thio, or —$NR^6$—.

The $R^4$ group in Formula I can be an alkyl, aryl, or aralkyl. Suitable alkyl groups typically contain no greater than 30 carbon atoms, no greater than 20 carbon atoms, no greater than 10 carbon atoms, no greater than 6 carbon atoms, or no greater than 4 carbon atoms. In some compounds, the alkyl group is methyl, ethyl, or propyl. Suitable aryl groups typically contain 6 to 30 carbon atoms, 6 to 24 carbon atoms, 6 to 18 carbon atoms, 6 to 12 carbon atoms, or 6 carbon atoms. In some compounds, the aryl group is phenyl. Suitable aralkyl groups typically contain an aryl group having 6 to 30 carbon atoms and an alkyl group having no greater than 30 carbon atoms. An example of an aralkyl group is 4-methyl-phenyl.

In other embodiments of Formula II, $R^4$ is a group $—N(R^5)_2$ where each $R^5$ are alkyl groups having no greater than 30 carbon atoms, no greater than 20 carbon atoms, no greater than 10 carbon atoms, no greater than 6 carbon atoms, or no greater than 4 carbon atoms. Alternatively, the two $R^5$ groups can combine together with the nitrogen atom to which they are attached to form a 4 to 8 membered ring structure. For example, the two $R^5$ groups can combine to form a five or six membered heterocyclic group having a nitrogen heteroatom.

In Formula I, $R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group. Exemplary structures include, but are not limited to the following:

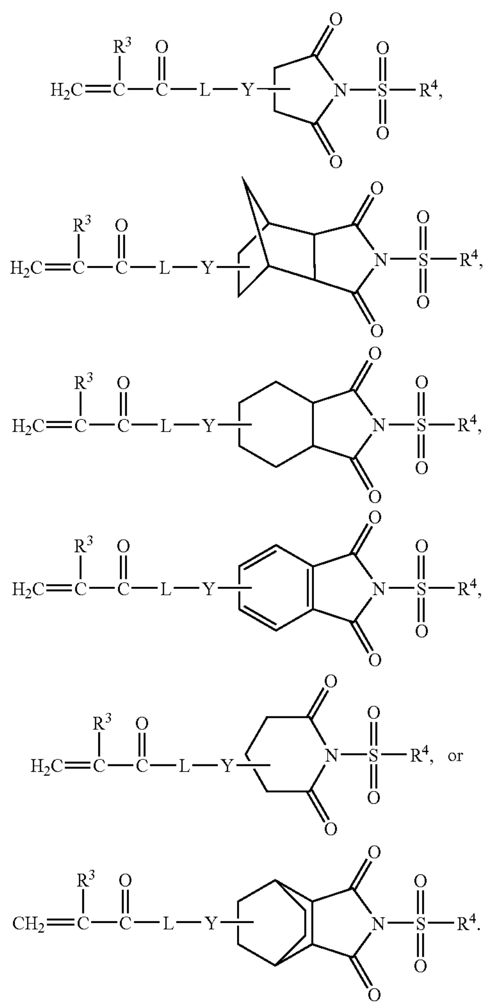

The groups $R^3$, $R^4$, L, and Y are the same as described above for Formula I. In these formulas, the group $CH_2{=}CR^3—CO-L-Y—$ can be attached to the ring structure in various locations, as indicated by the placement of this group within the ring structure. The monomers can be unsubstituted or substituted with a halo, alkyl, alkoxy, or combinations thereof.

Several factors can influence the selection of group Y for a particular application. These factors include, for example, ease of synthesis of the amine capture monomer, compatibility or reactivity of the amine capture monomer with the crosslinking monomer, and reactivity or selectivity of the amine capture group with an amine-containing material. For example, the size and the polarity of group Y can affect the reactivity of the amine capture group with amine-containing material. That is, varying the length and composition of group Y can alter the reactivity of the amine capture groups. Further, the size and nature of the ring structure containing the dicarboximide group can affect the surface concentration and reactivity with the amine-containing materials. The various groups in the amine capture monomer can be chosen, if desired, to provide a monomer that is liquid at ambient conditions. Liquid monomers tend to be useful in solventless coating compositions, which can be environmentally desirable.

The reaction mixtures are often coated from solution and dried (e.g., close to 100 percent solids) prior to polymerization. Solubility of the amine capture monomer in the solvent and miscibility with the crosslinking monomer can be important variables for obtaining suitable coatings. These factors can be controlled by selection of group Y. Heteroalkylene groups tend to improve solubility in polar solvents and monomers; alkylene groups tend to improve solubility in non-polar solvents and monomers.

Exemplary amine capture monomers of Formula I include, but are not limited to,

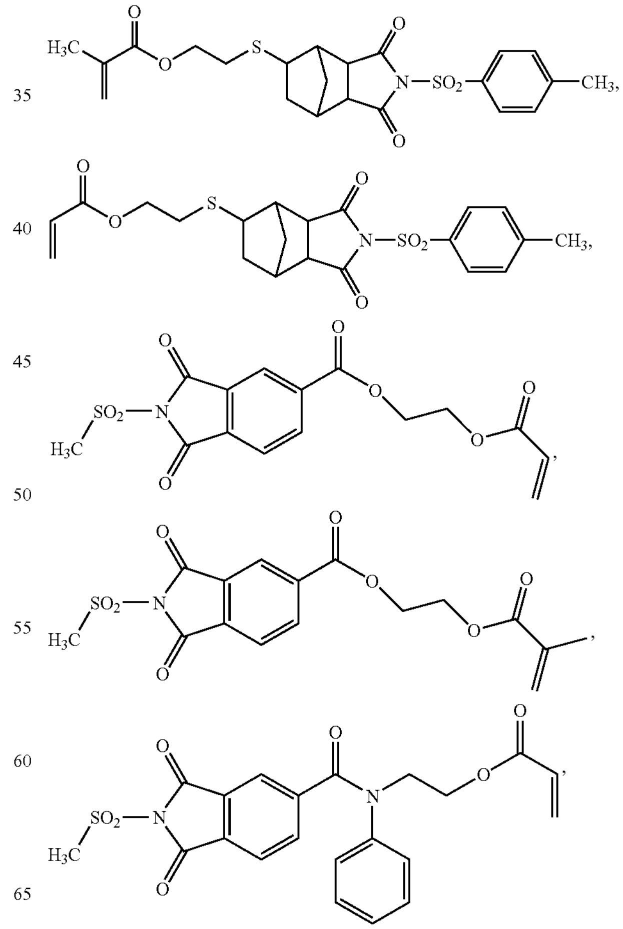

-continued

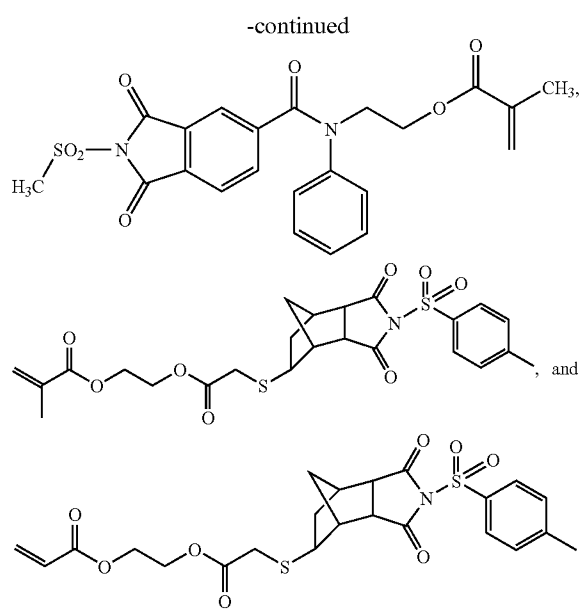

The amine capture monomers can be unsubstituted or substituted with a halo, alkyl, alkoxy, or combinations thereof.

The amine capture monomers contain two reactive functional groups: an amine reactive group that includes the N-sulfonyldicarboximide group and a (meth)acryloyl group that can undergo a free-radical polymerization reaction. Synthetic strategies must lead to these two reactive functional groups but be tolerant of their different reactivity. The compounds of Formula I may be prepared, for example, by reaction of a first compound having a nitrogen-containing group with a second compound containing a carboxylic acid anhydride. More specifically, the nitrogen-containing group of the first compound includes a nitrogen atom directly bonded to a sulfonyl group and to two hydrogen atoms. The second compound can also include a group —Y-L-CO—$CR^3$═$CH_2$. A typical synthesis approach is shown in Reaction Scheme A.

Reaction Scheme A

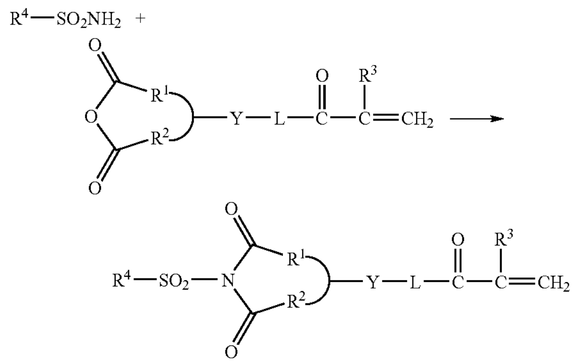

where $R^1$, $R^2$, $R^3$, $R^4$, Y, and L are the same as previously defined for Formula I.

The reaction mixture typically includes 0.1 to 90 weight percent of the amine capture monomer of Formula I based on the weight of monomers in the reaction mixture. If less than 0.1 weight percent amine capture monomer is included in the reaction mixture, there may not be a sufficient number of pendant amine capture groups in the resulting crosslinked polymeric material available for reaction with an amine-containing material. However, if the amount of amine capture monomer is greater than 90 weight percent, the crosslinked polymer may not be mechanically robust or dimensionally stable because of the low amount of crosslinking monomer in the reaction mixture.

The reaction mixture usually contains at least 0.1 weight percent, at least 0.5 weight percent, at least 1 weight percent, at least 2 weight percent, at least 5 weight percent, or at least 10 weight percent of the amine capture monomer of Formula I. The reaction mixture typically contains up to 90 weight percent, up to 80 weight percent, up to 70 weight percent, up to 60 weight percent, up to 50 weight percent, up to 40 weight percent, up to 30 weight percent, or up to 20 weight percent of the amine capture monomer. For example, the reaction mixture can contain 0.2 to 90 weight percent, 0.5 to 90 weight percent, 1 to 90 weight percent, 2 to 80 weight percent, 2 to 60 weight percent, 2 to 40 weight percent, 2 to 20 weight percent, or 2 to 10 weight percent of the amine capture monomer.

In addition to the monomer of Formula I, the reaction mixture contains a crosslinking monomer that includes at least two (meth)acryloyl groups. Suitable crosslinking monomers include di(meth)acrylates, tri(meth)acrylates, tetra (meth)acrylates, penta(meth)acrylates, and the like. These (meth)acrylates can be formed, for example, by reacting (meth)acrylic acid with an alkanediols, alkanetriols, alkanetetra-ols, or alkanepenta-ols.

Exemplary crosslinking monomers include 1,2-ethanediol di(meth)acrylate; 1,12-dodecanediol di(meth)acrylate; 1,4 butanediol di(meth)acrylate; 1,6-hexanediol di(meth)acrylate; trimethylolpropane triacrylate (e.g., commercially available under the trade designation TMPTA-N from Surface Specialties, Smyrna, Ga. and under the trade designation SR-351 from Sartomer, Exton, Pa.); pentaerythritol triacrylate (e.g., commercially available under the trade designation SR-444 from Sartomer); tris(2-hydroxyethylisocyanurate) triacrylate (commercially available under the trade designation SR-368 from Sartomer); a mixture of pentaerythritol triacrylate and pentaerythritol tetraacrylate (e.g., commercially available from Surface Specialties under the trade designation PETIA with an approximately 1:1 ratio of tetraacrylate to triacrylate and under the trade designation PETA-K with an approximately 3:1 ratio of tetraacrylate to triacrylate); pentaerythritol tetraacrylate (e.g., commercially available under the trade designation SR-295 from Sartomer); di-trimethylolpropane tetraacrylate (e.g., commercially available under the trade designation SR-355 from Sartomer); ethoxylated pentaerythritol tetraacrylate (e.g., commercially available under the trade designation SR-494 from Sartomer); and dipentaerythritol pentaacrylate (e.g., commercially available under the trade designation SR-399 from Sartomer). Mixtures of crosslinking monomers can be used.

The reaction mixture can contain 10 to 99.9 weight percent crosslinking monomer based on the weight of monomers in the reaction mixture. If less than this amount of crosslinking monomer is included in the reaction mixture, the resulting crosslinked polymeric material may not be mechanically robust or dimensionally stable. On the other hand, if a greater amount of crosslinking monomer is used, the number of pendant amine capture groups in the crosslinked polymeric material may be too low to efficiently react with amine-containing materials.

The amount of crosslinking monomer can be at least 10 weight percent, at least 15 weight percent, at least 20 weight percent, at least 30 weight percent, at least 40 weight percent, at least 50 weight percent, at least 60 weight percent, at least 70 weight percent, at least 80 weight percent, or at least 90 weight percent. For example, the amount of crosslinking monomer can be in the range of 10 to 99 weight percent, 20 to 90 weight percent, 30 to 90 weight percent, 30 to 80 weight percent, 30 to 70 weight percent, or 30 to 60 weight percent.

Other optional diluent monomers such as (meth)acrylates and (meth)acrylamides can be included in the reaction mixture. Suitable diluent monomers include monomers that do not have an amine capture group and that have only one (meth)acryloyl group. The reaction mixture can include up to 20 weight percent of the diluent monomer based on the weight of monomers in the reaction mixture. If more than about 20 weight percent diluent monomer is included in the reaction mixture, the crosslinked polymeric material may not be sufficiently mechanically robust and dimensionally stable or there may not be a sufficient number of pendant amine capture groups to effectively react with amine-containing compounds. In some reaction mixtures, no diluent monomer is included. The amount of diluent monomer typically is in the range of 0 to 20 weight percent, 0 to 15 weight percent, 0 to 10 weight percent, or 0 to 5 weight percent.

Some exemplary (meth)acrylate diluent monomers are alkyl (meth)acrylates such as methyl (meth)acrylate, ethyl (meth)acrylate, n-propyl (meth)acrylate, isopropyl (meth) acrylate, n-butyl (meth)acrylate, isobutyl (meth)acrylate, tert-butyl methacrylate, n-hexyl (meth)acrylate, cyclohexyl (meth)acrylate, 3,3,5-trimethylcyclohexyl (meth)acrylate, 2-methylbutyl (meth)acrylate, 2-ethylhexyl (meth)acrylate, 4-methyl-2-pentyl (meth)acrylate, n-octyl (meth)acrylate, isooctyl (meth)acrylate, n-decyl (meth)acrylate, isodecyl (meth)acrylate, lauryl (meth)acrylate, isononyl (meth)acrylate, isotridecyl (meth)acrylate, and behenyl (meth)acrylate.

Other exemplary (meth)acrylate diluent monomers are aryl (meth)acrylates such as phenyl (meth)acrylate, stearyl (meth) acrylate, and benzyl (meth)acrylate. Still other exemplary (meth)acrylate diluent monomers are hydroxy alkyl (meth) acrylates such as 2-hydroxyethyl (meth)acrylate and 3-hydroxypropyl (meth)acrylate, 4-hydroxybutyl (meth)acrylate, glycerol (meth)acrylate, and the like. Additional exemplary (meth)acrylate diluent monomers are ether-containing (meth) acrylates such as 2-ethoxyethyl (meth)acrylate, 2-methoxyethyl (meth)acrylate, polyethyleneglycol (meth)acrylate, and the like. The diluent monomers can be nitrogen-containing (meth)acrylates such as N,N-dimethylaminoethyl (meth) acrylate, N,N-dimethylaminopropyl (meth)acrylate, 2-trimethylammoniumethyl (meth)acrylate halides, and the like. The diluent monomers also can be (meth)acrylamides, N,N-dialkyl (meth)acrylamides, and the like.

Some reaction mixtures contain a solvent. Suitable solvents include, but are not limited to, water, acetonitrile, tetrahydrofuran, ethyl acetate, toluene, acetone, methyl ethyl ketone, isopropanol, N-methyl pyrrolidone, chlorinated and fluorinated hydrocarbons, fluorinated ethers, or combinations thereof. Other reaction mixtures can be solventless. Exemplary solventless reaction mixtures include those in which the amine capture monomer is a liquid or those in which the reaction mixture is a coated composition with the solvent removed.

A crosslinked polymeric material can be prepared that includes the reaction product of the reaction mixture, as described above, that contains (a) an amine capture monomer of Formula I and (b) a crosslinking monomer. These reaction mixtures are typically polymerized using a free radical polymerization method. There is often an initiator included in the reaction mixture. The initiator can be a thermal initiator, a photoinitiator, or both. The initiator is often used at a concentration of 0.1 to 5 weight percent, 0.1 to 3 weight percent, 0.1 to 2 weight percent, or 0.1 to 1 weight percent based on the weight of monomers in the reaction mixture.

When a thermal initiator is added to the reaction mixture, the crosslinked polymer can be formed at room temperature (i.e., 20 to 25 degrees Celsius) or at an elevated temperature. The temperature needed for polymerization often depends on the particular thermal initiator used. Examples of thermal initiators include organic peroxides or azo compounds.

When a photoinitiator is added to the reaction mixture, a crosslinked polymeric material can be formed by the application of actinic radiation until the composition gels or hardens. Suitable actinic radiation includes electromagnetic radiation in the infrared region, visible region, ultraviolet region, or a combination thereof.

Examples of photoinitiators suitable in the ultraviolet region include, but are not limited to, benzoin, benzoin alkyl ethers (e.g., benzoin methyl ether and substituted benzoin alkyl ethers such anisoin methyl ether), phenones (e.g., substituted acetophenones such as 2,2-dimethoxy-2-phenylacetophenone and substituted alpha-ketols such as 2-methyl-2-hydroxypropiophenone), phosphine oxides, polymeric photoinitiators, and the like.

Commercially available photoinitiators include, but are not limited to, 2-hydroxy-2-methyl-1-phenyl-propane-1-one (e.g., commercially available under the trade designation DAROCUR 1173 from Ciba Specialty Chemicals), a mixture of 2,4,6-trimethylbenzoyl-diphenyl-phosphine oxide and 2-hydroxy-2-methyl-1-phenyl-propan-1-one (e.g., commercially available under the trade designation DAROCUR 4265 from Ciba Specialty Chemicals), 2,2-dimethoxy-1,2-diphenylethan-1-one (e.g., commercially available under the trade designation IRGACURE 651 from Ciba Specialty Chemicals), a mixture of bis(2,6-dimethoxybenzoyl)-2,4,4-trimethyl-pentylphosphine oxide and 1-hydroxy-cyclohexyl-phenyl-ketone (e.g., commercially available under the trade designation IRGACURE 1800 from Ciba Specialty Chemicals), a mixture of bis(2,6-dimethoxybenzoyl)-2,4,4-trimethyl-pentylphosphine oxide (e.g., commercially available under the trade designation IRGACURE 1700 from Ciba Specialty Chemicals), 2-methyl-1[4-(methylthio)phenyl]-2-morpholinopropan-1-one (e.g., commercially available under the trade designation IRGACURE 907 from Ciba Specialty Chemicals), 1-hydroxy-cyclohexyl-phenyl-ketone (e.g., commercially available under the trade designation IRGACURE 184 from Ciba Specialty Chemicals), 2-benzyl-2-(dimethylamino)-1-[4-(4-morpholinyl)phenyl]-1-butanone (e.g., commercially available under the trade designation IRGACURE 369 from Ciba Specialty Chemicals), bis(2,4,6-trimethylbenzoyl)-phenylphosphine oxide (e.g., commercially available under the trade designation IRGACURE 819 from Ciba Specialty Chemicals), ethyl 2,4,6-trimethylbenzoyldiphenyl phosphinate (e.g., commercially available from BASF, Charlotte, N.C. under the trade designation LUCIRIN TPO-L), and 2,4,6-trimethylbenzoyidiphenylphosphine oxide (e.g., commercially available from BASF, Charlotte, N.C. under the trade designation LUCIRIN TPO).

Photoinitiators suitable for use in the visible region often include an electron donor, and electron acceptor such as an iodonium salt, and a visible light sensitizing compound such as an alpha di-ketone. Such photoinitiators are further described, for example, in U.S. Patent Pubiications 2005/0113477 A1 (Oxman et al.) and 2005/0070627 A1 (Falsafi et al.); and U.S. Pat. No. 6,765,036 B2 (Dede et al.), all incorporated herein by reference.

An article can be prepared that includes a substrate and a crosslinked polymeric material disposed on a surface of the substrate. The crosslinked polymeric material is often formed after coating a surface of the substrate with a reaction mixture that contains (a) an amine containing monomer of Formula I and (b) a crosslinking monomer that has at least two (meth) acryloyl groups.

The substrates can have any useful form including, but not limited to, films, sheets, membranes, filters, nonwoven or woven fibers, hollow or solid beads, bottles, plates, tubes, rods, pipes, or wafers. The substrates can be porous or non-porous, rigid or flexible, transparent or opaque, clear or colored, and reflective or non-reflective. The substrates can have a flat or relatively flat surface or can have a textured surface such as wells, indentations, channels, bumps, or the like. The substrates can have a single layer or multiple layers of material. Suitable substrate materials include, for example, polymeric materials, glasses, ceramics, metals, metal oxides, hydrated metal oxides, or combinations thereof.

Suitable polymeric substrate materials include, but are not limited to, polyolefins (e.g., polyethylene and polypropylene), polystyrenes, polyacrylates, polymethacrylates, polyacrylonitriles, polyvinyl acetates, polyvinyl alcohols, polyvinyl chlorides, polyoxymethylenes, polycarbonates, polyamides, polyimides, polyurethanes, phenolics, polyamines, amino-epoxy resins, polyesters, silicones, cellulose based polymers, polysaccharides, or combinations thereof.

Suitable glass and ceramic substrate materials can include, for example, silicon, aluminum, lead, boron, phosphorous, zirconium, magnesium, calcium, arsenic, gallium, titanium, copper, or combinations thereof. Glasses typically include various types of silicate containing materials.

In some embodiments, the substrate includes a layer of diamond-like glass as disclosed in U.S. Pat. No. 6,696,157 B1 (David et al.), the disclosure of which is incorporated herein by reference in its entirety. The diamond-like glass is an amorphous material that includes carbon, silicon, and one or more elements selected from hydrogen, oxygen, fluorine, sulfur, titanium, or copper. Some diamond-like glass materials are formed from a tetramethysilane precursor using a plasma process. A hydrophobic material can be produced that is further treated in an oxygen plasma to control the silanol concentration on the surface.

Suitable metals, metal oxides, or hydrated metal oxides for substrates can contain, for example, gold, silver, platinum, palladium, aluminum, copper, chromium, iron, cobalt, nickel, zinc, and the like. The metal-containing material can be alloys such as stainless steel, indium tin oxide, and the like. In some embodiments, a metal-containing material is the top layer of a multilayer substrate. For example, the substrate can have a polymeric second layer and a metal containing first layer. In one example, the second layer is a polymeric film and the first layer is a thin film of gold. In other examples, a multilayer substrate includes a polymeric film coated with a titanium-containing layer and then coated with a gold-containing layer. That is, the titanium layer can function as a tie layer or a primer layer for adhering the layer of gold to the polymeric film. In other examples of a multilayer substrate, a silicon support layer is covered with a layer of chromium and then with a layer of gold. The chromium layer can improve the adhesion of the gold layer to the silicon layer.

The articles can be prepared by providing a substrate, disposing a reaction mixture on a surface of the substrate, and curing the reaction mixture to form a crosslinked polymeric material. The reaction mixture contains (a) an amine capture monomer of Formula I and (b) a crosslinking monomer, as described above. The reaction mixture can be cured, for example, through the application of heat (i.e., a thermal initiator is used) or through the application of actinic radiation (i.e., a photoinitiator is used).

The reaction mixture can often wet the surface of the substrate and the resulting crosslinked polymer adheres to the surface of the substrate. The crosslinked polymer usually adheres without the formation of a covalent bond between a reactive group on the polymer and a complementary group on the surface of the substrate. Rather, the polymer adheres by interlocking with surface imperfections on the substrate.

In some articles, the crosslinked polymeric material is patterned on the substrate. Any suitable pattern of the crosslinking polymeric material can be formed. For example, the pattern can be in the form of text, design, image, or the like. The pattern can be, for example, in the form of dots, squares, rectangles, circles, lines, or waves (e.g., square waves, sinusoidal waves, and saw tooth waves).

One method of forming a patterned crosslinked polymeric layer includes disposing a pattern of the reaction mixture on the surface of the substrate by screen printing, jet printing (e.g., spray jet, valve jet, or ink jet printing), and the like. Useful devices forjet printing are described, for example, in U.S. Pat. No. 6,513,897 (Tokie) and in U.S. Patent Publication No. 2002/0128340 (Young et al.), both incorporated herein by reference. After application of the pattern to the surface of the substrate, the reaction mixture can be cured. For example, the reaction mixture can be cured by application of heat if a thermal initiator is included in the reaction mixture or by application of actinic radiation if a photoinitiator is included in the reaction mixture.

Another method of forming a patterned crosslinked polymeric layer includes forming a layer of the reaction mixture on the substrate, curing a first portion of the reaction mixture to form a pattern of crosslinked polymeric material on the substrate, and removing a second portion of the reaction mixture that is not cured. The layer of reaction mixture on the substrate can be prepared using any suitable technique such as, for example, brush coating, spray coating, gravure coating, transfer roll coating, knife coating, curtain coating, wire coating, and doctor blade coating.

One method of polymerizing a portion of the reaction mixture involves the use of a photoinitiator in the reaction mixture and the use of masks. The mask contains a pattern of openings and can be positioned between the layer of reaction mixture and the actinic radiation source. Actinic radiation can pass through the openings in the mask. Upon exposure to actinic radiation, a first portion of the reaction mixture layer corresponding to the openings in the mask can polymerize and a second portion of the reaction mixture layer that is blocked from the actinic radiation by the mask remains uncured or not reacted. That is, the uncured reaction mixture is a monomeric composition that has not gelled or hardened to form a crosslinked polymeric material. The uncured reaction mixture can be removed using a suitable solvent for the monomers of Formula I, the crosslinking monomers, and any optional diluent monomers. The solvent typically does not dissolve the cured crosslinked polymeric material because of the extensive crosslinking. Thus, the uncured reactive mixture can be removed leaving a pattern of crosslinked polymeric material on the substrate surface.

Suitable solvents for removing the unreacted reaction mixture include, but are not limited to, water, acetonitrile, tetrahydrofuran, ethyl acetate, toluene, acetone, methyl ethyl ketone, isopropanol, N-methyl pyrrolidone, chlorinated and fluorinated hydrocarbons, fluorinated ethers, or combinations thereof. The crosslinked polymeric material is typically insoluble in these solvents. As used herein, an insoluble polymer is one that has a solubility at room temperature that is less than 0.01 weight percent in a solvent such as, for example, water, acetonitrile, tetrahydrofuran, ethyl acetate, toluene, acetone, methyl ethyl ketone, isopropanol, N-methyl pyrrolidone, chlorinated and fluorinated hydrocarbons, fluorinated ethers, or combinations thereof.

Suitable masks for this method of patterning include polymeric materials (e.g., polyesters such as polyethylene terephthalate or polyethylene naphthalate, polyimide, polycarbonate, or polystyrene), metal foil materials (e.g., stainless steel, other steels, aluminum, or copper), paper, woven or nonwoven fabric materials, or combinations thereof. Polymeric masks and the openings in these masks are further described in U.S. Pat. No. 6,897,164 B2 (Baude et al.), incorporated herein by reference. The openings in the mask can be of any suitable dimension.

The crosslinked polymeric material has pendant amine capture groups. Thus, an article having a layer or pattern of crosslinked polymeric material on a surface of a substrate can have amine capture groups that are capable of reacting with an amine-containing material. The pendant amine capture groups of the polymeric material are of Formula II

II

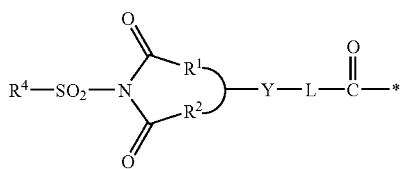

attached to the backbone of the crosslinked polymeric backbone. The groups L, Y, $R^1$, $R^2$ and $R^4$ are previously described for Formula I. The asterisk in Formula II indicates the location where the pendant amine capture group is attached to the backbone of the crosslinked polymeric material. The pendant amine capture groups include a N-sulfonyldicarboximide group.

The pendant groups according to Formula II usually have improved hydrolytic stability compared to derivatives of N-hydroxysuccinimide, which are groups known to react with amine-containing materials. Because of the improved hydrolytic stability of the pendant groups of Formula II, the crosslinked polymeric materials and articles containing the crosslinked polymeric material typically can be used in aqueous systems.

The amine capture groups can be reacted with an amine-containing material resulting in the immobilization of the amine-containing material. A method of immobilizing an amine-containing material includes providing a substrate, and disposing a reaction mixture on a surface of the substrate. The reaction mixture contains (a) a monomer of Formula I and (b) a crosslinking monomer that includes at least two (meth)acryloyl groups. The method further includes curing the reaction mixture to form a crosslinked polymeric material having a pendant amine capture group, and reacting an amine-containing material with the pendant amine capture group of the crosslinked polymeric material. In this method, the N-sulfonyldicarboximide group in the pendant amine capture group can react with an amine-containing material. In some embodiments, the amine-containing materials are biological materials such as, for example, amino acid, peptide, DNA, RNA, protein, enzyme, organelle, cells, tissue, immunoglobin, or a fragment thereof. In other embodiments, the amine-containing material is a non-biological amine such as an amine-containing analyte.

The amine-containing material can react with the pendant amine capture group by a ring opening reaction with the N-sulfonyldicarboximide group. The amine-containing material can have a primary amine group or a secondary amine group. For example, the amine-containing material can be a primary amine-containing biological material of formula $H_2N$-T where T is the remainder of the primary amine-containing biological material (i.e., the group T is equal to a primary amine-containing biological material of formula $H_2N$-T minus the —$NH_2$ group). Group T often has an alkylene group attached directly to the —$NH_2$ group. The primary amine-containing biological material reacts with the crosslinked polymeric material having pendant groups of Formula II to produce a crosslinked polymeric material having a reacted pendant group of Formula III:

III

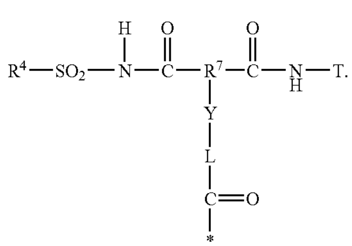

In Formula III, $R^7$ is an alkylene having 1 to 5 carbon atoms, aromatic group, saturated or unsaturated cyclic group, saturated or unsaturated bicyclic group, or combination thereof. $R^7$ corresponds to the combined groups $R^1$ and $R^2$ in Formulas I and II. The group L, Y, $R^4$, and * are the same as previously defined for Formulas I and II. The presence of the immobilized amine can be determined, for example, using mass spectroscopy, contact angle measurement, infrared spectroscopy, and ellipsometry. Additionally, various immunoassays and optical microscopic techniques can be used if the amine-containing material is a biologically active material.

The rate of reaction of amine-containing materials with the N-sulfonyldicarboximide groups of the pendant amine capture groups of Formula II is typically faster than the rate of hydrolysis of the N-sulfonyidicarboximide group. That is, immobilization of amine-containing materials occurs at a faster rate than the hydrolysis reactions. The amine-containing materials are not easily displaced once immobilization to a pendant group of the crosslinked polymeric material has occurred due to the formation of a covalent carbonylimino bond.

Immobilized biological amine-containing materials can be useful in the medical diagnosis of a disease or of a genetic defect. The immobilized amine-containing materials can also be used for biological separations or for detection of the presence of various biomolecules. Additionally, the immobilized amine-containing materials can be used in bioreactors or as biocatalysts to prepare other materials. The pendant groups with the N-sulfonylaminocarbonyl groups also can be used to detect amine-containing analytes that are not biological materials. The amine-containing analytes can have primary amine groups, secondary amine groups, or a combination thereof.

Other materials can be further bound to the immobilized amine-containing material. This further bound material can be associated with the amine-containing material before immobilization of the amine-containing material or can be bound to the amine-containing material subsequent to immobilization of the amine-containing material. The amine-containing material and the further bound material can be complementary RNA fragments, complementary DNA fragments, an antigen-antibody combination, an immunoglobin-bacterium combination, and the like.

Biological amine-containing materials often can remain active after attachment to the pendant group of the crosslinked polymeric material (i.e., the pendant groups according to Formula III can include biologically active amine-containing materials). For example, an immobilized antibody can subsequently bind to an antigen or an immobilized antigen can subsequently bind to an antibody. Similarly an immobilized amine-containing biological material that has a portion that can bind to a bacterium can subsequently bind to the bacterium (e.g., an immobilized immunoglobulin can subsequently bind to a bacterium such as *Staphylococcus aureus*).

The pendant groups of Formula II and Formula III are attached to the backbone of a crosslinked polymeric material. The crosslinked polymeric material is formed by a free radical polymerization reaction of (meth)acryloyl groups. A crosslinked polymeric material with pendant groups of Formula II can be further crosslinked by reaction of a primary amine containing material having at least two primary amine groups, secondary amine groups, or a combination thereof. That is, an amine containing material that has more than one primary amine or secondary amine groups may react with more than one pendant group of Formula II.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Table of Abbreviations

| Abbreviation or Trade Designation | Description |
|---|---|
| ACN | Acetonitrile |
| DMF | Dimethylformamide |
| NMP | N-methylpyrrolidinone |
| THF | Tetrahydrofuran |
| TMPTA | Trimethylolpropane triacrylate |
| Photoinitiator | DAROCUR 1173 Photo curing agent 2-hydroxy-2-methyl-1-phenyl-1-propanone, available from Ciba; Hawthorne, NJ |
| DI water | Deionized water |
| PEI | Polyethyleneimine |
| IPA | Isopropyl alcohol |
| TWEEN-25 | Polyoxyethylenesorbitan monolaurate from Sigma, St Louis, MO |

Preparative Example 1

Preparation of

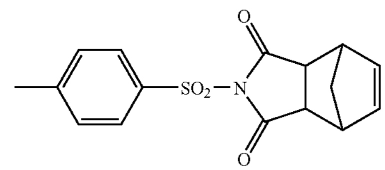

A 3-neck round bottom flask, fitted with a magnetic stir bar, an addition funnel and a hose adapter that was connected to a source of nitrogen gas, was charged with a 60 weight percent dispersion of NaH in mineral oil (9.45 g) and hexane (20 mL). The mixture was stirred for approximately 15 minutes after which DMF (100 mL) was added to the flask. A mixture of p-toluenesulfonamide (15.7 g) and 5-norbornene-2,3-dicarboxylic anhydride (16.2 g) in DMF (100 mL) was slowly added to the flask from the addition funnel. The mixture was allowed to stir overnight at room temperature. An additional solution of 5-norbornene-2,3-dicarboxylic anhydride (1.6 g) in DMF (10 mL) was added dropwise to the flask and the mixture was stirred for approximately 6 hours. Acetic anhydride (28.14 g) was then added to the flask and the mixture was stirred overnight. Aqueous $NaHCO_3$ solution was then added to the flask, followed by aqueous HCl. The mixture was filtered and the filtered solid was dried overnight using a vacuum oven. The solid was then recrystallized from methanol to afford 14.8 g of product.

Preparative Example 2

Preparation of

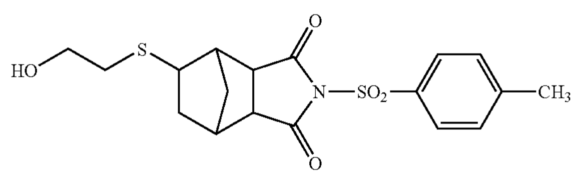

A mixture of 2-mercaptoethanol (1.69 grams), the N-(4-methylbenzenesulfonyl)succinimide product of Preparative Example 1 (7.0 grams), VAZO 64 (0.2 grams), and ethyl acetate (8.7 grams) was purged with nitrogen gas for approximately 15 minutes and was then heated at 55° C. under a nitrogen atmosphere for 24 hours. The solution was allowed to cool to room temperature, during which time white crystals precipitated. The crystals were isolated by filtration, washed with ethyl acetate and dried to afford 3.2 grams of product.

Preparative Example 3

Preparation of

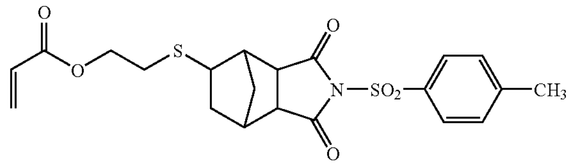

To a magnetically stirred mixture of the alcohol product of Preparative Example 2 (5.0 grams), NMP (20 milliliters), and triethylamine (1.5 grams) within a round bottom flask there is slowly added acryloyl chloride (1.25 grams) over about 15 minutes. The mixture is stirred overnight at room temperature under a nitrogen atmosphere, after which time the mixture is poured into 0.1N aqueous HCl (100 milliliters) in a beaker. This mixture is extracted with ethyl acetate and then the ethyl acetate mixture is dried over sodium sulfate. The volatile components are then removed using a rotary evaporator to afford the product.

Preparative Example 4

Preparation of

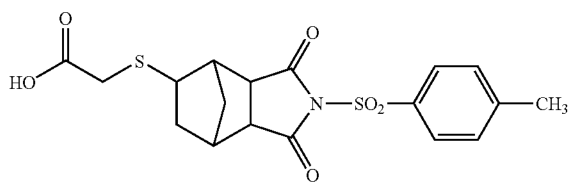

A solution of the N-(4-methylbenzenesulfonyl)dicarboximide product of Preparative Example 1 (25.0 g) and mercaptoacetic acid (7.63 g) in ethyl acetate (161 g) within a 3-neck round bottom flask was purged with nitrogen gas for 10 minutes. The flask was fitted with a reflux condenser and a magnetic stir bar. Azobis(isobutyronitrile) (0.0484 g) was added to the flask and the mixture was stirred and heated at 55° C. for sixteen hours. After the mixture had cooled to room temperature, the solvent was removed using a rotary evaporator. The brown solid was recrystallized from toluene/acetonitrile to give 11.9 g of product.

Preparative Example 5

Preparation of

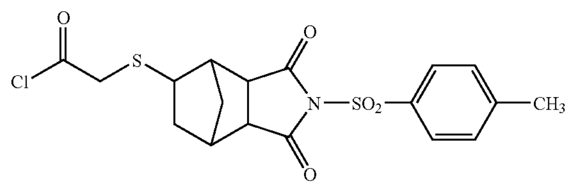

A mixture of the carboxy-containing product of Preparative Example 4 (5.06 g), thionyl chloride (1.62 g), DMF (1 drop), and chloroform (61.8 g) was made within a 100 mL round bottom flask. The flask was fitted with a magnetic stir bar and a reflux condenser and then the mixture was stirred and heated under reflux for two hours. The mixture was allowed to cool to room temperature and then heptane was added to the flask until the product precipitated. The mixture was filtered and the product was dried in a vacuum oven to give 4.8 g of product.

Preparative Example 6

Preparation of

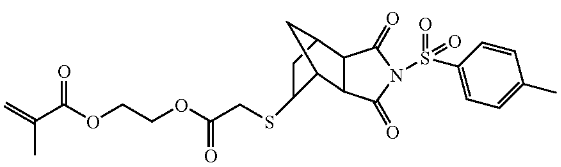

To a round bottom flask fitted with a magnetic stirrer was added ethyl acetate (0.25 milliliter), 2-hydroxyethyl methacrylate (0.10 gram) and N-ethyldiisopropylamine (0.12 gram). The product of Preparative Example 5 (0.30 gram) was dissolved in ethyl acetate (1.75 milliliter) and added to the flask under a nitrogen atmosphere and left to stir at room temperature overnight. After which time was added ethyl acetate (10 milliliter). The mixture was poured into 0.1N aqueous HCl (10 milliliter) in a beaker. The aqueous layer was separated and the organic phase was washed with 0.1N aqueous HCl (10 milliliter), followed by a saturated sodium chloride solution (10 milliliter). The ethyl acetate mixture was dried over magnesium sulfate. A rotary evaporator was used to concentrate the mixture, which was purified on an Analogix Flash Chromatography system over 20 minutes with a gradient from 35:63 to 85:15 of ethyl acetate and hexanes. The fractions containing the desired product were collected and the volatile components were then removed using a rotary evaporator to afford 0.2178 gram of product, a yield of 59%.

Preparative Example 7

Preparation of

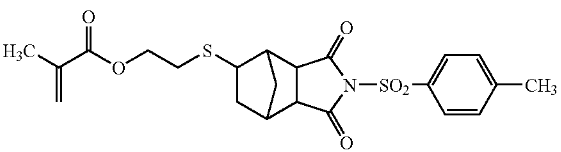

To a magnetically stirred mixture of the alcohol product of Preparative Example 2 (5.0 grams), NMP (20 milliliters), and triethylamine (1.5 grams) within a round bottom flask there is slowly added methacrylic anhydride (2.12 grams) over about15 minutes. The mixture is stirred overnight at room temperature under a nitrogen atmosphere, after which time the mixture is poured into 0.1N aqueous HCl (100 milliliters) in a beaker. This mixture is extracted with ethyl acetate and then the ethyl acetate mixture is dried over sodium sulfate. The volatile components are then removed using a rotary evaporator to afford the product.

Preparative Example 8

Preparation of

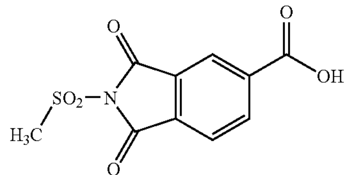

A mixture of methanesulfonamide (10 grams), 1,2,4-benzenetricarboxylic anhydride (26.3 grams), triethylamine (37.2 grams), and DMF (84.6 grams) was magnetically stirred under a nitrogen atmosphere overnight at room temperature. The mixture was then heated to 50° C. and stirred at this temperature for 30 minutes, after which time it was allowed to cool to room temperature and was filtered. The solid was recrystallized from glacial acetic acid and the white crystalline solid was filtered, washed with diethyl ether, and dried to afford 5.4 grams of product.

Preparative Example 9

Preparation of

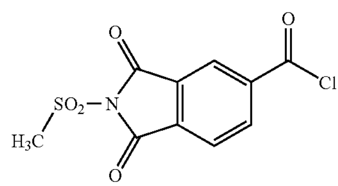

A mixture of the carboxylic acid product of Preparative Example 8, (3.0 grams), thionyl chloride (1.72 grams), DMF (1 drop), and ACN (18.9 grams) within a round bottom flask fitted with a reflux condenser was magnetically stirred under a nitrogen atmosphere at reflux for 1 hour. The volatile components were then removed using a rotary evaporator and the partially solid residue in the flask was washed into a fritted glass funnel with diethyl ether. The solid was washed with diethyl ether and was dried under a flow of nitrogen gas to afford 2.9 grams of product.

Preparative Example 10

Preparation of

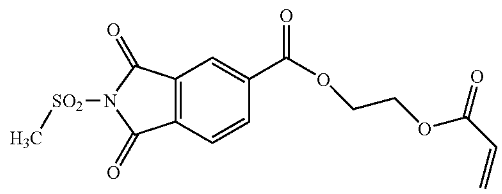

A mixture of the carbonyl chloride product of Preparative Example 9 (5.0 grams), NMP (20 milliliters), 2-hydroxyethyl acrylate (1.97 grams), and triethylamine (1.89 grams) within a round bottom flask is magnetically stirred overnight under a nitrogen atmosphere at room temperature. The mixture is then poured into 0.1N aqueous HCl (100 milliliters) in a beaker. This mixture is extracted with ethyl acetate and then the ethyl acetate mixture is dried over sodium sulfate. The volatile components are then removed using a rotary evaporator to afford the product.

Preparative Example 11

Preparation of

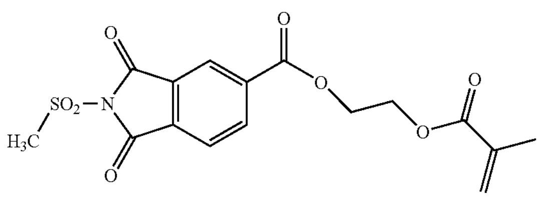

A mixture of the carbonyl chloride product of Preparative Example 9 (1.06 grams), acetonitrile (5.5 milliliters), 2-hydroxyethyl methacrylate (0.51 grams), and ethyidiisopropylamine (0.62 grams) within a round bottom flask was magnetically stirred overnight under a nitrogen atmosphere at room temperature. The mixture was concentrated on a rotary evaporator. The resulting oil was taken up in chloroform (25 milliliters) then washed with 0.1N HCl (25 milliliters) and dried over magnesium sulfate. The chloroform was removed resulting in an oil that was taken up in hot methanol. Upon cooling a dark oil settled and the clear solution was decanted, concentrated on a rotary evaporator. The resulting oil was dissolved in hot isopropyl alcohol, upon cooling to room temperature a white crystalline solid precipitated, which was filtered, washed with chilled IPA and dried in an oven to provide 81 milligrams of desired product.

Preparative Example 12

Preparation of

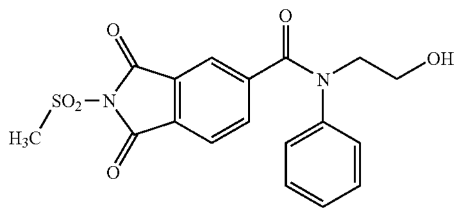

A mixture of the carbonyl chloride product of Preparative Example 9 (5.0 grams), NMP (20 milliliters) N-phenylethanolamine (2.34 grams), and triethylamine (1.89 grams) within a round bottom flask is magnetically stirred overnight under a nitrogen atmosphere at room temperature. The mixture is then poured into 0.1N aqueous HCl (100 milliliters) in a beaker. This mixture is extracted with ethyl acetate and then the ethyl acetate mixture is dried over sodium sulfate. The volatile components are then removed using a rotary evaporator to afford the product.

Preparative Example 13

Preparation of

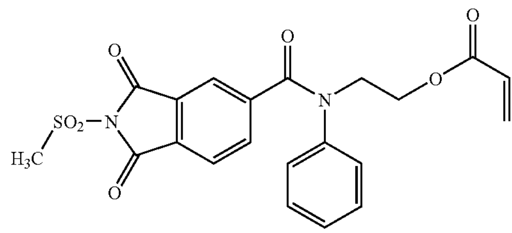

A mixture of the alcohol product of Preparative Example 12 (5.0 grams), NMP (20 milliliters), acryloyl chloride (1.18 grams), and triethylamine (1.45 grams) within a round bottom flask is magnetically stirred overnight under a nitrogen atmosphere at room temperature. The mixture is then poured into 0.1N aqueous HCl (100 milliliters) in a beaker. This mixture is extracted with ethyl acetate and then the ethyl acetate mixture is dried over sodium sulfate. The volatile components are then removed using a rotary evaporator to afford the product.

Preparative Example 14

Preparation of

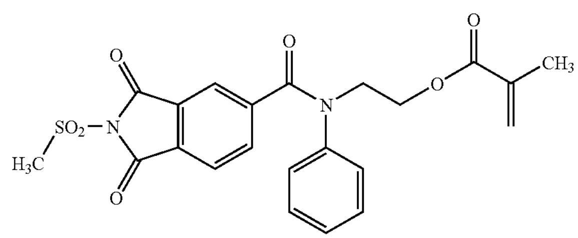

A mixture of the alcohol product of Preparative Example 12 (5.0 grams), NMP (20 milliliters), methacrylic anhydride (2.00 grams), and triethylamine (1.45 grams) within a round bottom flask is magnetically stirred overnight under a nitrogen atmosphere at room temperature. The mixture is then poured into 0.1N aqueous HCl (100 milliliters) in a beaker. This mixture is extracted with ethyl acetate and then the ethyl acetate mixture is dried over sodium sulfate. The volatile components are then removed using a rotary evaporator to afford the product.

Preparative Example 15

Preparation of:

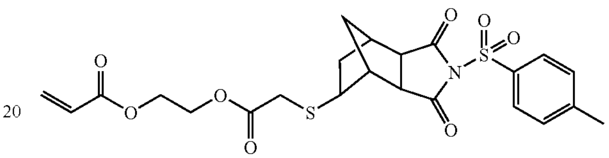

To a round bottom flask fitted with a magnetic stirrer was added ethyl acetate (0.25 mL), 2-hydroxyethyl methacrylate (0.10 g) and N-ethyldiisopropylamine (0.12 g). The product of Preparative Example 5 (0.30 g) was dissolved in ethyl acetate (1.75 mL) and added to the flask under a nitrogen atmosphere and left to stir ambient overnight. After which time was added ethyl acetate (10 mL). The mixture was poured into 0.1N aqueous HCl (10 mL) in a beaker. The aqueous layer was separated and the organic phase was washed with 0.1N aqueous HCl (10 mL), followed by a saturated sodium chloride solution (10 mL). The ethyl acetate mixture was dried over magnesium sulfate. A rotary evaporator was used to concentrate the mixture, which was purified on an Analogix Flash Chromatography system over 20 minutes with a gradient from 35:63 to 85:15 of ethyl acetate and hexanes. The fractions containing the desired product were collected and the volatile components were then removed using a rotary evaporator to afford 0.2178 g of product, a yield of 59%.

Preparation of PEI Coated Glass Slide Matrix

Glass microscope slides were soaked for two hours in a 5 Molar NaOH bath; rinsed with DI water, ethanol, and methanol; and dried under a stream of nitrogen. The clean slides were kept in an 80° C. oven until needed.

Eight of the slides were arranged in a matrix of 2 columns and 4 rows. The slides were secured in position within the matrix using a strip of tape down the middle of the back side of each slide. A 2 weight percent solution of PEI in IPA was coated onto the matrix using a number 12 Mayer rod. The coating was allowed to dry in air.

Preparation of IgG Labeled with Cy5

The contents of three vials of Cy5 dye (3H-Indolium, 2-[5-[1-[6-[(2,5-dioxo-1-pyrrolidinyl)oxy]-6-oxohexyl]-1,3-dihydro-3,3-dimethyl-5-sulfo-2H-indol-2-ylidene]-1,3-pentadienyl]-1-ethyl-3,3-dimethyl-5-sulfo-, inner salt (9CI)) were dissolved in dimethylsulfoxide (DMSO) to a total volume of 100 microliters. The vials of Cy5 dye were obtained from GE-Amersham Biosciences, Piscataway N.J. The resulting dye solution was added to 1 milliliter of a 5 milligrams/milliliter solution of mouse IgG in 0.1 M sodium carbonate (at pH 9.0). The mouse IgG was obtained from Sigma, St. Louis, Mo. The resulting solution was protected from light exposure and gently rocked for 45 minutes at room temperature. This solution contained Cy5-labelled antibody and unreacted Cy5.

Cy5-labelled antibody (Cy5-IgG) was separated from unreacted Cy5 label using gel filtration chromatography. The solution containing the Cy5-IgG and unreacted CyS was added to a PD-10 column that was equilibrated using phosphate buffer solution (PBS) at pH 7.4. The PD-10 column was obtained from GE-Amersham Biosciences, Piscataway N.J. The Cy5-IgG fraction was collected by washing with PBS at pH 7.4. The Cy5/ IgG ratio was calculated by measuring the IgG concentration (280 nm) and the Cy5 concentration (650 nm) in the Cy5-IgG fraction. The product specifications provided by the manufacturer of Cy5 and IgG were followed to obtain the extinction coefficient values for IgG and Cy5 as well as the absorbance contribution from covalently bound Cy5 at 280 nm. The final CyS-IgG solution had a concentration 1.3 milligrams/milliliter Cy5-IgG with a Cy5/IgG ratio of 2.2. From this stock solution, test solutions containing 130, 50, 13 and 5 micrograms/milliliters of Cy5-IgG in 10 millimolar carbonate buffer at pH 9.6 were prepared. The buffer was prepared using sodium carbonate/sodium bicarbonate buffer capsules available from Sigma, St. Louis, Mo.

Comparative Example C1

A solution of Photoinitiator (0.01 gram) and TMPTA (0.6 gram) in ACN (5 grams) was prepared. This solution contained 11 weight percent TMPTA and 0.18 weight percent Photoinitiator based on the weight of the solution. This solution was coated onto a PEI coated glass slide matrix, which is described above, using a number 12 Mayer rod. The coating was allowed to dry in air. The coated matrix was passed twice through a curing apparatus at a rate of 50 feet/minute (15 meters/minute). The curing apparatus was obtained from Fusion Systems of Gaithersburg, Md. and was equipped with a F300 lamp. The resulting cured coating was rubbed with a metal spatula to ensure the coating could not be rubbed off.

Spots of 5 microliters of the Cy5-IgG test solutions prepared above and a sample without Cy5-IgG were applied to the coated surface and allowed to sit for 30 minutes. The surface was rinsed with 0.25 weight percent TWEEN-25 in DI water and then rinsed with DI water. The slides were dried under nitrogen and placed into a fluorescence reader, which is commercially available from Tecan Group LTD, Research Triangle Park, N.C. under the trade designation LS SERIES TECAN. Single scan measurements were made by adjusting the focal height to 1002 micrometers, 40 micrometers resolution, oversampling of 3 micrometers, a gain of 160, and a pinhole depth focus of ±150 micrometers. The data was analyzed as 16-bit pixelized TIFF files using software commercially available from Molecular Devices Corp, Sunnyvale, Calif. under the trade designation GENEPIX PRO. The data are shown in Table 1.

Example 1

A solution was prepared by dissolving the material from Preparative Example 6 (0.031 gram), Photoinitiator (0.009 gram), and TMPTA (0.54 gram) in ACN (5.2 grams). The resulting solution contained 0.5 weight percent Preparative Example 1, 0.18 weight percent Photoinitiator, and 10 weight percent TMPTA based on the weight of the solution. This solution was coated onto a PEI coated glass slide matrix described above, using a number 12 Mayer rod. The resulting coating was allowed to dry in air. The coated matrix was passed twice at a rate of 50 feet/minute (15 meters/minute) through the Fusion Systems curing apparatus equipped with a F300 lamp. The resulting cured coating was rubbed with a metal spatula to ensure the coating could not be rubbed off.

Five microliter spots of the Cy5-IgG test solutions and of a sample without Cy5-IgG were made onto the coated surface and allowed to sit for 30 minutes. The surface was rinsed with 0.25 weight percent TWEEN-25 in DI water and then with DI water. The slides were dried under nitrogen and placed into a fluorescence reader, which is commercially available from Tecan Group LTD, Research Triangle Park, N.C. under the trade designation LS SERIES TECAN. Single scan measurements were made by adjusting the focal height to 1002 micrometers and using 40 micrometers resolution, a gain of 160, oversampling of 3 micrometers, and a pinhole depth focus of ±150 micrometers. The data was analyzed as 16-bit pixelized TIFF files using software commercially available from Molecular Devices Corp, Sunnyvale, Calif. under the trade designation GENEPIX PRO. The data are shown in Table 1.

Example 2

A solution was prepared by dissolving the material of Preparative Example 11 (0.032 gram), Photoinitiator (0.009 gram), and TMPTA (0.56 gram) in ACN (5.3 grams). The resulting solution contained 0.5 weight percent Preparative Example 2, 0.18 weight percent photoinitiator, and 10 weight percent TMPTA based on the weight of the solution. This solution was coated onto a PEI coated glass slide matrix described above using a number 12 Mayer rod. The resulting coating was allowed to dry in air.

The coated matrix was passed twice through the Fusion Systems curing apparatus equipped with a F300 lamp at a rate of 50 feet/minute (15 meters/minute). The resulting cured coating was rubbed with a metal spatula to ensure the coating could not be rubbed off.

Five microliter spots of the Cy5-IgG test solutions and of a sample without Cy5-IgG were applied to the coated surface and allowed to sit for 30 minutes. The surface was rinsed with 0.25 weight percent TWEEN-25 in DI water and then with DI water. The slides were dried under nitrogen and placed into a fluorescence reader, which is commercially available from Tecan Group LTD, Research Triangle Park, N.C. under the trade designation LS SERIES TECAN. Single scan measurements were made by adjusting the focal height to 1002 micrometers and using 40 micrometers resolution, a gain of 160, oversampling of 3 micrometers, and a pinhole depth focus of ±150 micrometers. The data was analyzed as 16-bit pixelized TIFF files using software commercially available from Molecular Devices Corp, Sunnyvale, Calif. under the trade designation GENEPIX PRO. The data are shown in Table 1.

TABLE 1

| Concentration of Cy5-IgG (Micrograms/milliliter) | Fluorescence Measurement Example C1 | Fluorescence Measurement Example 1 | Fluorescence Measurement Example 2 |
|---|---|---|---|
| 130 | 34108 | 65535 | 65535 |
| 50 | 17295 | 58371 | 36596 |
| 13 | 8135 | 42565 | 13915 |
| 5 | 1270 | 18540 | 4079 |
| 0 | 1266 | 288 | 1400 |

*Note the value of 65535 is the maximum number of pixels that can be measured using a 16-bit fluorescence reader.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A reaction mixture comprising:

a) an amine capture monomer of Formula I

I

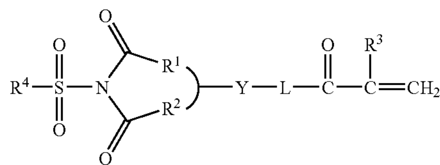

wherein

L is an oxy or —$NR^6$—;

$R^1$ and $R^2$ together with a dicarboximide group to which they are attached form a four to eight membered heterocyclic or heterobicyclic group that can be fused to an optional aromatic group, optional saturated or unsaturated cyclic group, or optional saturated or unsaturated bicyclic group;

$R^3$ is hydrogen or methyl;

$R^4$ is an alkyl, aryl, aralkyl, or —$N(R^5)_2$ wherein each $R^5$ is an alkyl group or both $R^5$ groups taken together with the nitrogen atom to which they are attached form a four to eight membered heterocyclic group;

$R^6$ is hydrogen, alkyl, aryl, aralkyl, acyl, alkylsulfonyl, or arylsulfonyl;

Y is a single bond or a divalent group comprising an alkylene, heteroalkylene, arylene, or combinations thereof;

the amine capture monomer is unsubstituted or substituted with a halo, alkyl, alkoxy, or combinations thereof; and b) a crosslinking monomer comprising at least two (meth) acryloyl groups.

2. The reaction mixture of claim 1, wherein the amine capture monomer is of Formula I(a)

I(a)

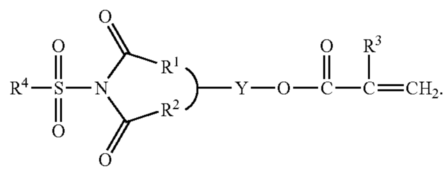

3. The reaction mixture of claim 1, wherein the amine capture monomer is of Formula I(b)

I(b)

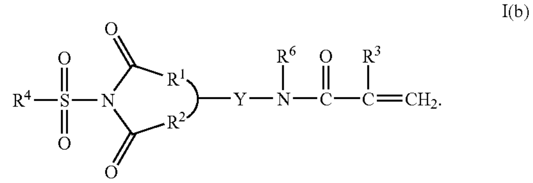

4. The reaction mixture of claim 1, wherein the amine capture monomer is of formula

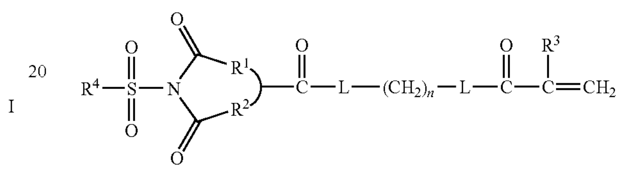

wherein n is an integer of 1 to 30.

5. The reaction mixture of claim 1, wherein the amine capture monomer is of formula

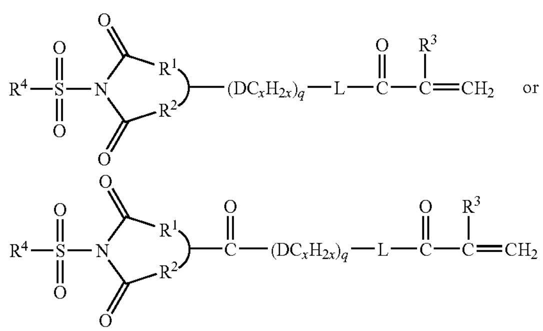

wherein q is an integer of 1 to 15;

x is an integer of 2 to 4; and

D is oxy, thio, or —NH—.

6. The reaction mixture of claim 1, wherein the amine capture monomer is of formula

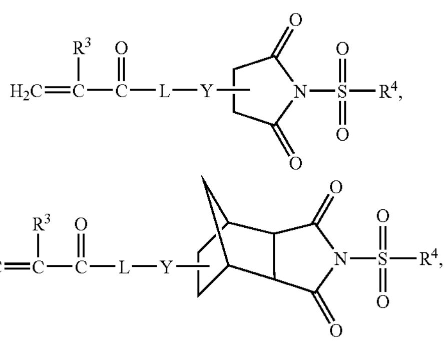

-continued

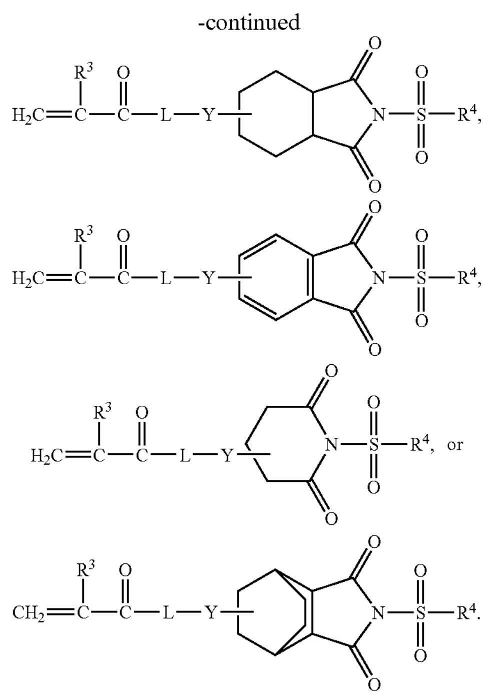

7. The reaction mixture of claim 1, wherein the amine capture monomer comprises

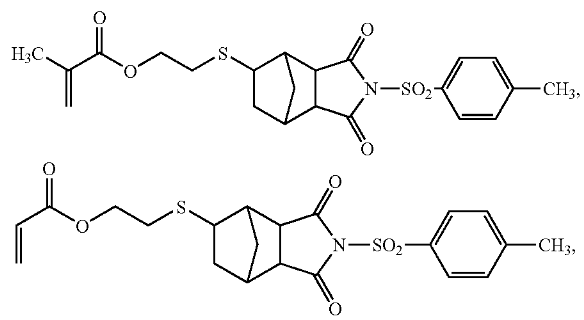

-continued

8. The reaction mixture of claim 1, further comprising a photoinitiator, a thermal initiator, or a combination thereof.

9. The reaction mixture of claim 1, wherein Y further comprises a carbonyl, carbonyloxy, carbonylimino, oxy, thio, —$NR^6$—, or combinations thereof.

10. The reaction mixture of claim 1, wherein the reaction mixture comprises 0.1 to 50 weight percent of the amine capture monomer of Formula I based on the weight of the monomers in the reaction mixture.

* * * * *